US011887458B2

(12) United States Patent
Lin et al.

(10) Patent No.: US 11,887,458 B2
(45) Date of Patent: Jan. 30, 2024

(54) FALL DETECTION SYSTEM

(71) Applicant: NATIONAL CHENG KUNG UNIVERSITY, Tainan (TW)

(72) Inventors: Chih-Lung Lin, Tainan (TW); Wen-Ching Chiu, Tainan (TW); Yuan-Hao Ho, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 35 days.

(21) Appl. No.: 17/813,609

(22) Filed: Jul. 20, 2022

(65) Prior Publication Data

US 2022/0358824 A1 Nov. 10, 2022

Related U.S. Application Data

(62) Division of application No. 17/142,250, filed on Jan. 6, 2021, now Pat. No. 11,450,192.
(Continued)

(30) Foreign Application Priority Data

Dec. 1, 2020 (TW) ................. 109142228

(51) Int. Cl.
*G08B 21/04* (2006.01)
*G06F 3/01* (2006.01)
(Continued)

(52) U.S. Cl.
CPC .............. *G08B 21/043* (2013.01); *A43B 3/34* (2022.01); *G06F 3/011* (2013.01); *G06V 40/103* (2022.01); *G06V 40/23* (2022.01)

(58) Field of Classification Search
CPC ........ G08B 21/043; A43B 3/34; G06V 40/23; G06F 3/011
See application file for complete search history.

(56) References Cited

U.S. PATENT DOCUMENTS 6,016,707 A   1/2000  Lin et al.
7,592,944 B2  9/2009  Fullerton et al.
(Continued)

FOREIGN PATENT DOCUMENTS

CN   205656739 U   10/2016
CN   106725507 A    5/2017
(Continued)

OTHER PUBLICATIONS

Daquan Feng et al., "Kalman-Filter-Based Integration of IMU and UWB for High-Accuracy Indoor Positioning and Navigation," IEEE Internet of Things Journal, Apr. 2020, pp. 3133-3146, vol. 7, No. 4.
(Continued)

*Primary Examiner* — Albert K Wong
(74) *Attorney, Agent, or Firm* — CKC & Partners Co., LLC

(57) ABSTRACT

A fall detection system includes first sensing devices, second sensing devices, positioning modules, a data server and a display device. The first sensing device is configured to detect a posture of a body part of a user for obtaining body part posture data. The positioning modules are configured to detect positions of the first and second sensing devices, so as to obtain corresponding body part position data. Each of the second sensing devices is disposed on a shoe to detect a posture of a user's feet and to measure a distance from an ambient object for obtaining feet posture data and distance measurement data. The data server is configured to receive the body part posture data, the body part position data, the feet posture data and the distance measurement data to determine if the user falls down.

8 Claims, 13 Drawing Sheets

Related U.S. Application Data

(60) Provisional application No. 62/958,286, filed on Jan. 7, 2020, provisional application No. 62/957,329, filed on Jan. 6, 2020.

(51) Int. Cl.
*A43B 3/34* (2022.01)
*G06V 40/20* (2022.01)
*G06V 40/10* (2022.01)

(56) References Cited

U.S. PATENT DOCUMENTS

| | | | |
|---|---|---|---|
| 8,428,696 | B2 | 4/2013 | Foo |
| 8,502,729 | B2 | 8/2013 | Leach, Jr. et al. |
| 9,377,857 | B2 | 6/2016 | Geisner et al. |
| 9,568,594 | B2 | 2/2017 | Harash et al. |
| 10,050,650 | B2 | 8/2018 | O'Hagan et al. |
| 10,210,737 | B2 | 2/2019 | Zhao |
| 10,495,725 | B2 | 12/2019 | Zhang et al. |
| 10,685,237 | B1 | 6/2020 | Mirza et al. |
| 10,825,315 | B2 | 11/2020 | Hanson et al. |
| 10,930,131 | B2 | 2/2021 | Stut et al. |
| 11,083,652 | B2* | 8/2021 | Bogie ............ A61G 5/128 |
| 11,158,179 | B2 | 10/2021 | Tunnell |
| 11,181,378 | B2* | 11/2021 | Couvet ............ A43B 3/34 |
| 11,298,050 | B2 | 4/2022 | Ikeda |
| 11,622,721 | B1* | 4/2023 | Matak ............ G01L 5/0095 340/870.07 |
| 11,683,614 | B2* | 6/2023 | Case, Jr. ............ G06Q 30/0639 340/870.07 |
| 2013/0100268 | A1 | 4/2013 | Mihailidis et al. |
| 2014/0118498 | A1* | 5/2014 | Lee ............ G08B 21/02 348/46 |
| 2018/0233018 | A1 | 8/2018 | Burwinkel et al. |
| 2019/0054347 | A1 | 2/2019 | Saigh et al. |
| 2019/0385476 | A1 | 12/2019 | Sadeghi |
| 2020/0046262 | A1 | 2/2020 | Annegarn et al. |
| 2020/0205697 | A1 | 7/2020 | Zheng et al. |
| 2020/0289027 | A1 | 9/2020 | Naveh et al. |
| 2021/0019505 | A1 | 1/2021 | Varsanik et al. |
| 2021/0104264 | A1 | 4/2021 | Bose et al. |
| 2021/0150872 | A1 | 5/2021 | Ten Kate et al. |
| 2021/0153814 | A1 | 5/2021 | Demazumder |
| 2021/0205660 | A1 | 7/2021 | Shavit |
| 2021/0321222 | A1 | 10/2021 | Lagace et al. |
| 2022/0101710 | A1 | 3/2022 | Tunnell |

FOREIGN PATENT DOCUMENTS

| | | |
|---|---|---|
| CN | 107123239 A | 9/2017 |
| CN | 108171931 A | 6/2018 |
| TW | 331125 U | 5/1998 |
| TW | 333823 U | 6/1998 |
| TW | 351174 U | 1/1999 |
| TW | 410602 U | 11/2000 |
| TW | 477711 B | 3/2002 |
| TW | 201700025 A | 1/2017 |
| TW | 201704771 A | 2/2017 |
| TW | M538211 U | 3/2017 |
| TW | I635415 B | 9/2018 |
| TW | I656502 B | 4/2019 |
| WO | 2015027955 A1 | 3/2015 |
| WO | 2016174662 A1 | 11/2016 |

OTHER PUBLICATIONS

Paul K. Yoon et al., "Robust Biomechanical Model-Based 3-D Indoor Localization and Tracking Method Using UWB and IMU," IEEE Sensors Journal, Feb. 15, 2017, pp. 1084-1096, vol. 17, No. 4.

William Suski et al., "Using a Map of Measurement Noise to Improve UWB Indoor Position Tracking," IEEE Transactions on Instrumentation and Measurement, Aug. 2013, pp. 2228-2236, vol. 62, No. 8.

Zhendong Yin et al., "WUB-IP: A High-Precision UWB Positioning Scheme for Indoor Multiuser Applications," IEEE Systems Journal, Mar. 2019, pp. 279-288, vol. 13, No. 1.

Mi-Kyung Oh et al., "Traffic-Reduced Precise Ranging Protocol for Asynchronous UWB Positioning Networks," IEEE Communications Letters, May 2010, pp. 432-434, vol. 14, No. 5.

Nan Bai et al., "A High-Precision and Low-Cost IMU-Based Indoor Pedestrian Positioning Technique," IEEE Sensors Journal, Jun. 15, 2020, pp. 6716-6726, vol. 20, No. 12.

Wala Saadeh et al., "A Patient-Specific Single Sensor IoT-Based Wearable Fall Prediction and Detection System," IEEE Transactions on Neural Systems and Rehabilitation Engineering, May 2019, pp. 995-1003, vol. 27, No. 5.

Lina Tong et al., "HMM-Based Human Fall Detection and Prediction Method Using Tri-Axial Accelerometer," IEEE Sensors Journal, May 2013, pp. 1849-1856, vol. 13, No. 5.

Shaghayegh Zihajehzadeh et al., "UWB-Aided Inertial Motion Capture for Lower Body 3-D Dynamic Activity and Trajectory Tracking," IEEE Transactions on Instrumentation and Measurement, Dec. 2015, pp. 3577-3587, vol. 64, No. 12.

Mostafa Elhoushi et al., "Motion Mode Recognition for Indoor Pedestrian Navigation Using Portable Devices," IEEE Transactions on Instrumentation and Measurement, Jan. 2016, pp. 208-221, vol. 65, No. 1.

Illapha Cuba Gyllensten et al., "Identifying Types of Physical Activity With a Single Accelerometer: Evaluating Laboratory-trained Algorithms in Daily Life," IEEE Transactions on Biomedical Engineering, Sep. 2011, pp. 2656-2663, vol. 58, No. 9.

Maja Stikic et al., "Weakly Supervised Recognition of Daily Life Activities with Wearable Sensors," IEEE Transactions on Pattern Analysis and Machine Intelligence, Dec. 2011, pp. 2521-2537, vol. 33, No. 12.

Yuan-Hao Ho et al., "High-Precision UWB Indoor Positioning System for Customer Pathway Tracking," 2019 IEEE 8th Global Conference on Consumer Electronics, Oct. 15-18, 2019.

Chih-Lung Lin et al., "Fall Monitoring for the Elderly Using Wearable Inertial Measurement Sensors on Eyeglasses," IEEE Sensors Letters, 2017, vol. 2, No. 3.

Abdulrahman Alarifi et al., "Ultra Wideband Indoor Positioning Technologies: Analysis and Recent Advances," Sensors, May 16, 2016, vol. 16, 707.

H. A. Shaban et al., "Localization with Sub-Millimeter Accuracy for UWB-Based Wearable Human Movement Radar Systems," Journal of Electromagnetic Waves and Applications, 2011, pp. 1633-1644, vol. 25.

Chih-Lung Lin et al., "Innovative Head-Mounted System Based on Inertial Sensors and Magnetometer for Detecting Falling Movements," Sensors, Oct. 12, 2020, vol. 20, 5774.

"Taiwan Patient-safety Reporting system," Annual Report 2018, Ministry of Health and Welfare, R.O.C. (Taiwan), Joint Commission of Taiwan.

Sung-Yen Chang, Abstract of "Study on Fall-detection Using Multiple Sensors," PhD Dissertation of National Cheng Kung University, 2012.

* cited by examiner

Plane Classification

FALL DETECTION SYSTEM

CROSS-REFERENCE TO RELATED APPLICATIONS

This application is a Divisional Application of U.S. application Ser. No. 17/142,250 filed Jan. 6, 2021, which claims priority to Taiwan Application Serial Number 109142228, filed Dec. 1, 2020, U.S. provisional Application Ser. No. 62/958,286, filed Jan. 7, 2020 and U.S. provisional Application Ser. No. 62/957,329, filed Jan. 6, 2020, which are herein incorporated by reference.

BACKGROUND

Field of Invention

The present disclosure relates to a fall detection system.

Description of Related Art

Fall accidents often result in serious body injuries and sequelae to the elderly and lower the mobility of the elderly, and thus mobility aids are needed to help the mobility of the elderly. Under severe conditions, the elderly people who fall may be paralyzed and cannot move freely. As such, care attendants are needed to take care of the paralyzed elder, thus consuming much social resource.

SUMMARY

Embodiments of the disclosure provide a fall detection system to detect if a user falls down or is at an about-to-fall (fall-like) status, thereby alleviating burdens of care attendants.

According to an embodiment of the disclosure, the fall detection system includes plural wearable devices, plural positioning devices, a data server and a display device. The wearable devices are disposed on plural body parts of the user, in which each wearable device has a sensing device. The sensing device includes a posture detection device and a communication device. The posture detection device is configured to detect a body part posture of the user, thereby obtaining a set of body part posture data. The communication device is configured to transmit the set of body part posture data. The positioning devices are disposed in the activity space to detect a 3D position of each wearable device, thereby enabling each wearable device to obtain a set of body part position data. The data server is configured to receive the set of body part posture data and the set of body part position data corresponding to each wearable device, thereby computing skeleton information of the user, and to compute body posture information of the user according to the skeleton information, and then to perform a fall detection operation to determine if the user falls down according to the body posture information, wherein the data server issues a fall detection signal when it is determined that the user falls down. The display device configured to receive the fall detection signal and display a warning message in accordance with the fall detection signal.

In some embodiments, the display device is a smart watch, a smart glass, a notebook computer, a tablet computer or a personal digital assistant (PDA).

In some embodiments, the data server is further configured to provide a set of space risk level data, the set of space risk level data comprising a plurality of risk levels in respective sub-spaces of the activity space, wherein the fall detection operation determines if the user falls down according to the body posture information, a space position of the user and the set of space risk level data.

According to another embodiment of the disclosure, the fall detection system includes plural sensing devices, a data server and a display device. Each sensing device is disposed on a sensing position of a shoe of the user, and includes a ranging device and a communication device. The ranging device is configured to measure a distance between the sensing position and an ambient object, thereby obtaining a set of distance measurement data. The communication device is configured to transmit the set of distance measurement data. The data server configured to receive the set of distance measurement data of each of the sensing devices, and to perform a fall detection operation to determine if the user falls down according to the set of distance measurement data, wherein the data server issues a fall detection signal when it is determined that the user falls down. The display device is configured to receive the fall detection signal and display a warning message in accordance with the fall detection signal.

In some embodiments, a first one of the sensing devices is disposed on a toe of the shoe of the user, a second one of the sensing devices is disposed on a heel of the shoe of the user, a third one of the sensing devices is disposed on a front sole of the shoe of the user, and a fourth one of the sensing devices is disposed on a rear sole of the shoe of the user.

In some embodiments, a first one of the sensing devices is disposed on a toe of the shoe of the user, a second one of the sensing devices is disposed on a left front sole of the shoe of the user, a third one of the sensing devices is disposed on a right front sole of the shoe of the user, a fourth one of the sensing devices is disposed adjacent the second one and the third one of the sensing devices, a fifth one of the sensing devices is disposed on a rear sole of the shoe of the user, a sixth one of the sensing devices is disposed on a lateral side of the shoe of the user, a seventh one of the sensing devices is disposed on a heel of the shoe of the user, and the fourth one of the sensing devices is disposed among the fifth one, the second one and the third one of the sensing devices.

According to another embodiment of the disclosure, the fall detection system includes plural first wearable devices, plural second wearable devices, plural positioning devices, a data server and a display device. The first wearable devices are disposed on plural body parts of the user, in which each first wearable device has a first sensing device. The first sensing device includes a first posture detection device and a first communication device. The first posture detection device is configured to detect a body part posture of the user, thereby obtaining a set of body part posture data. The first communication device is configured to transmit the set of body part posture data. Each second wearable device is disposed on a foot of the user and has plural second sensing devices. Each second sensing device is disposed on a sensing position of the foot, and includes a second posture detection device, a ranging device and a second communication device. The second posture detection device is configured to detect a foot posture of the user, thereby obtaining a set of foot posture data. The ranging device is configured to measure a distance between the sensing position and an ambient object, thereby obtaining a set of distance measurement data. The second communication device is configured to transmit the set of foot posture data and the set of distance measurement data. The positioning devices are disposed in the activity space to detect a 3D position of each of the first wearable devices and the second wearable devices, thereby enabling each of the first wearable devices and the second wearable devices to obtain a set of body part position data. The data server is configured to compute skeleton information of the user according to the set of body part position and the set of body part posture data corresponding to each of the first wearable devices and the set of body part position and the set of foot posture data corresponding to each of the second wearable devices, and to compute body posture information of the user according to the skeleton information, and then to perform a fall detection operation to determine if the user falls down according to the body posture information, and the set of foot posture data and the set of distance measurement data of each of the second sensing devices, wherein the data server issues a fall detection signal when it is determined that the user falls down. The display device is configured to receive the fall detection signal and to display a warning message in accordance with the fall detection signal.

In some embodiments, the display device is a smart watch or a smart glass.

In some embodiments, the data server is further configured to provide a set of space risk level data, the set of space risk level data comprising a plurality of risk levels in respective sub-spaces of the activity space, wherein the fall detection operation determines if the user falls down according to the body posture information, a space position of the user, the set of space risk level data, and the set of foot posture data and the set of distance measurement data of each of the second sensing devices.

In some embodiments, a first one of the second sensing devices is disposed on a toe of the shoe of the user, a second one of the second sensing devices is disposed on a heel of the shoe of the user, a third one of the second sensing devices is disposed on a front sole of the shoe of the user, and a fourth one of the second sensing devices is disposed on a rear sole of the shoe of the user.

In some embodiments, each second wearable device is a shoe.

BRIEF DESCRIPTION OF THE DRAWINGS

The invention can be more fully understood by reading the following detailed description of the embodiment, with reference made to the accompanying drawings as follows.

DESCRIPTION OF THE PREFERRED EMBODIMENTS

Figure 1A:
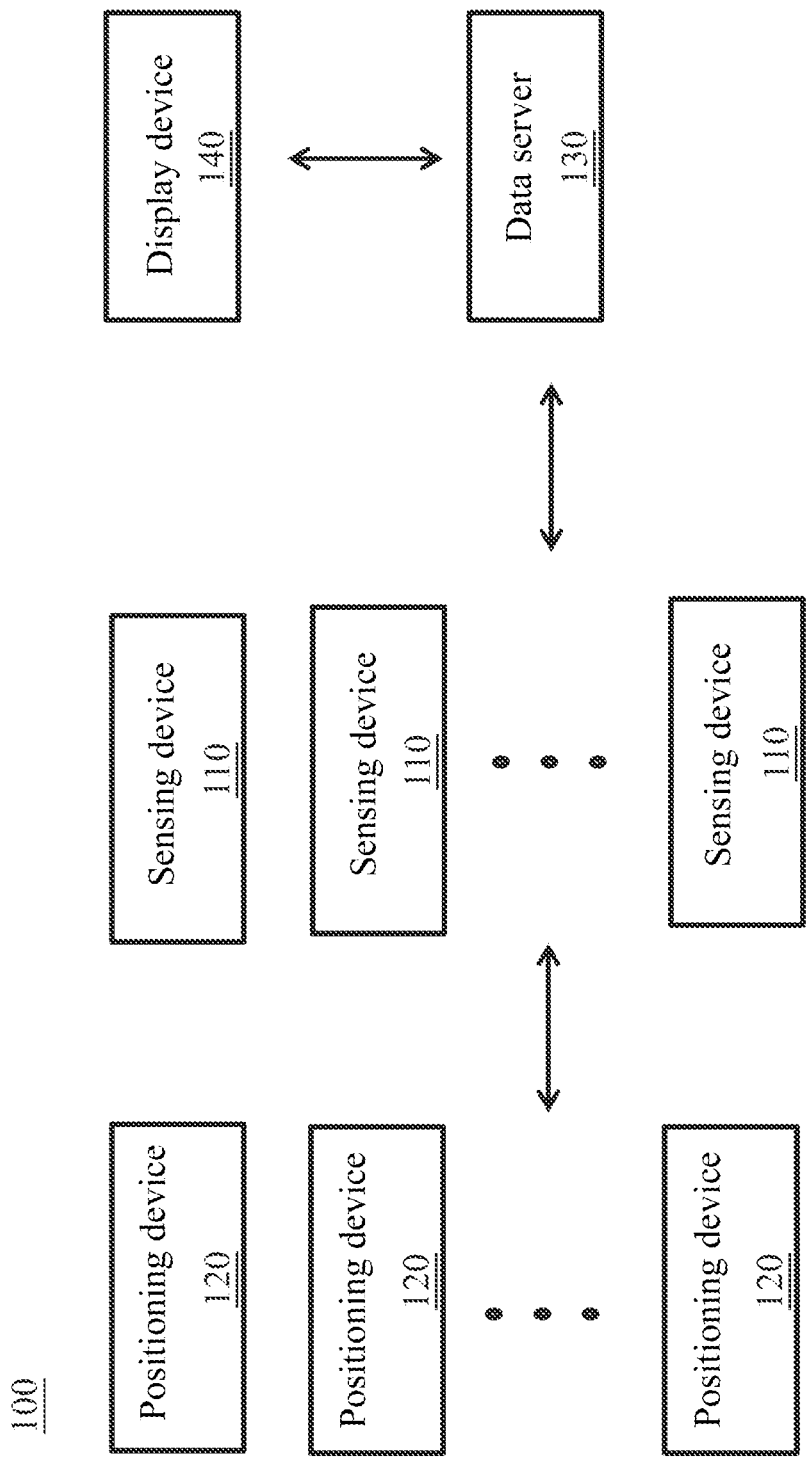
FIG. 1A is a schematic block diagram of a fall detection system according to some embodiments of the disclosure.

Reference will now be made in detail to the embodiments of the present invention, examples of which are illustrated in the accompanying drawings. Wherever possible, the same reference numbers are used in the drawings and the description to refer to the same or like parts.

As used herein, the terms "first" and "second" do not intend to indicate a specific order or sequence, and are merely used for distinguishing the devices or operations described by similar phraseology or terminology herein.

Referring to FIG. 1A, FIG. 1A is a schematic block diagram of a fall detection system according to some embodiments of the disclosure. A fall detection system 100 includes plural sensing devices 110, plural positioning devices 120, a data server 130 and a display device 140. The sensing devices 110 are disposed on a wearable device, thereby allowing a user to carry the sensing devices conveniently. In the embodiments, the wearable device may be a wrist ring, an ankle ring, eyeglasses, a neck ring, a neck chain, an earphone, an eardrop, a head band, a hair band, a hat, a belt buckle, a waist belt, a key chain, a knee support, and a shoe, etc. However, embodiments of the disclosure are not limited thereto. The sensing devices 110 may have different functions in accordance with their corresponding wearable devices. For example, in the embodiments, the sensing devices 110 include a first sensing device 112 and a second sensing device 114 which have different functions.

Figure 1B:
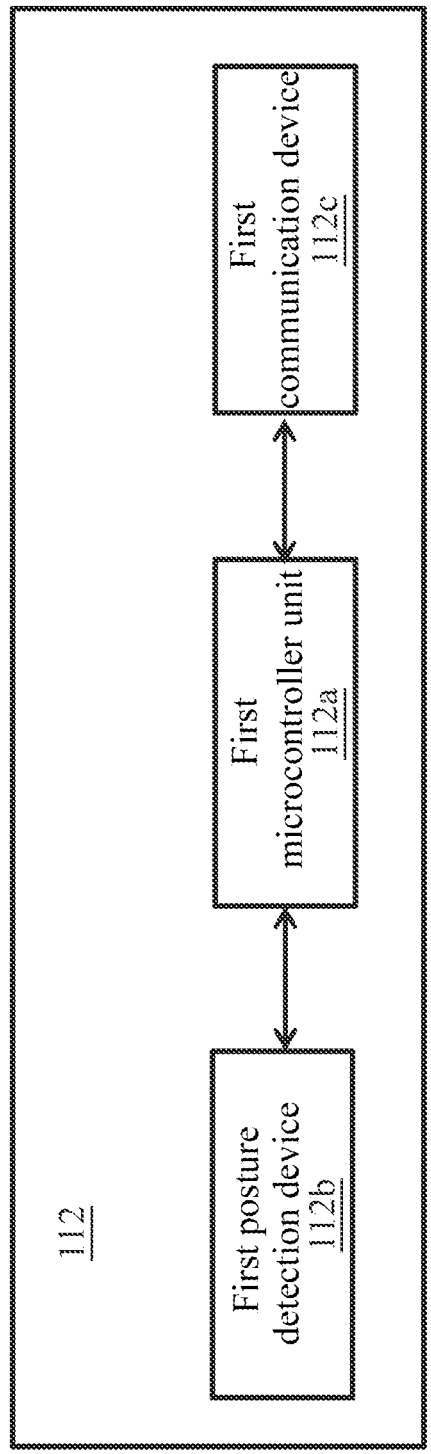
FIG. 1B is schematic block diagram of a first sensing device according to some embodiments of the disclosure.

Referring to FIG. 1B, FIG. 1B is schematic block diagram of a first sensing device 112 according to some embodiments of the disclosure. The first sensing device 112 includes a first microcontroller unit 112a, a first posture detection device 112b and a first communication device 112c. The first microcontroller unit 112a is used to control the first posture detection device 112b and the first communication device 112c. The first posture detection device 112b is used to detect a body part posture of the user, thereby obtaining a set of body part posture data. The first communication device 112c is used to transmit the set of body part posture data.

For example, when being disposed on a hand band, the first sensing device 112 can sense (or detect) a posture of a user's head, and sends a set of body part posture data of the user's head to the data server 130. For example, when being disposed on a belt buckle, the first sensing device 112 can sense (or detect) a posture of a user's trunk, and sends a set of body part posture data of the user's trunk to the data server 130. For example, when being disposed on a wrist ring, the first sensing device 112 can sense (or detect) a posture of a user's hand, and sends a set of body part posture data of the user's hand to the data server 130. For example, when being disposed on an ankle ring, the first sensing device 112 can sense (or detect) a posture of a user's foot, and sends a set of body part posture data of the user's foot to the data server 130.

In the embodiments of the disclosure, a user may wear various wearable devices on his or her various body parts, such that the first sensing devices 112 on the wearable devices can sense the postures of the body parts and sends sets of posture data of the body parts to the data server 130. In the embodiments of the disclosure, the first sensing devices 112 may include an accelerator, a gyroscope, a magnetometer and/or a barometer for detecting postures of the user's body parts, and the first communication devices 112c on the wearable devices can send the sets of posture data of the user's body parts to the data server 130 by using a WiFi technique or an ultra-wideband (UWB) technique. However, embodiments of the disclosure are limited thereto. On the other hand, the reading values of the barometers may be converted to altitude information of the first sensing devices 112.

Figure 1C:
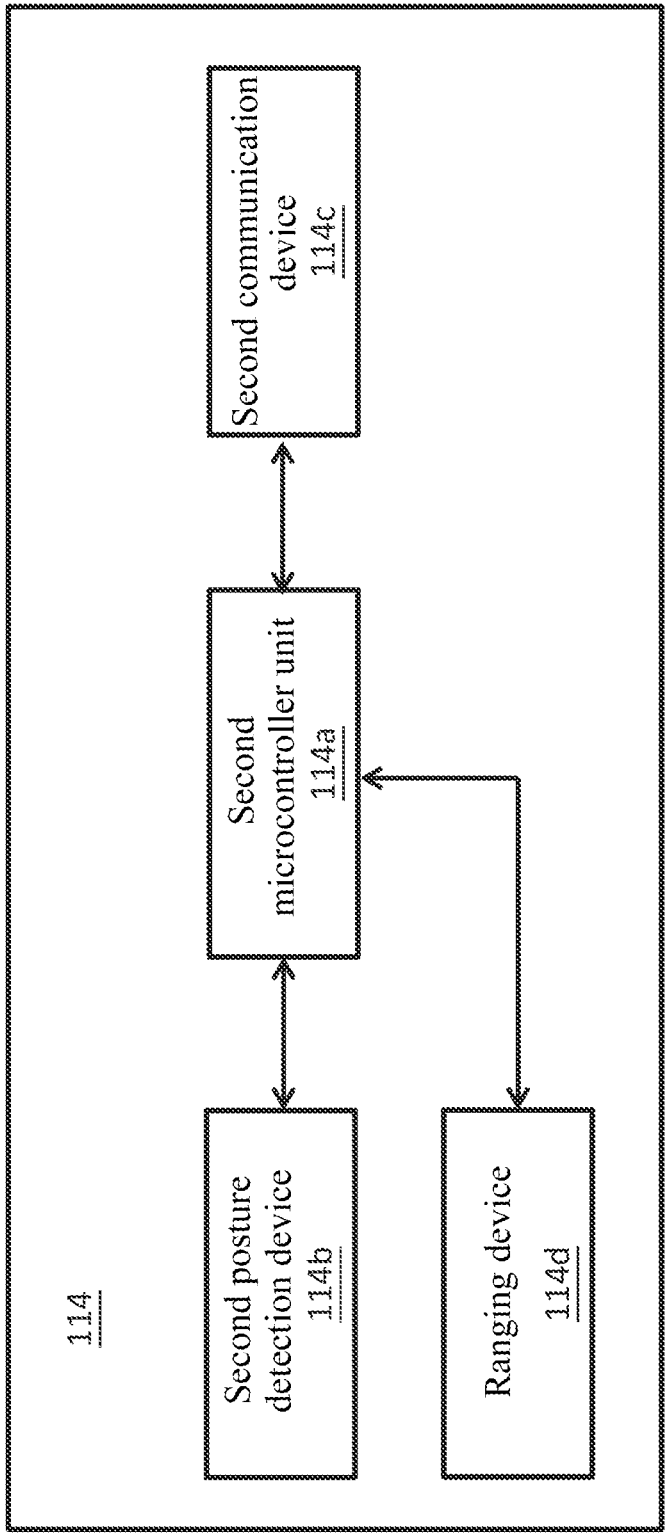
FIG. 1C is schematic block diagram of a second sensing device according to some embodiments of the disclosure.

Referring to FIG. 1C, FIG. 1C is schematic block diagram of a second sensing device 114 according to some embodiments of the disclosure. The second sensing device 114 includes a second microcontroller unit 114a, a second posture detection device 114b, a second communication device 114c, and a ranging device 114d. In the embodiments, the second sensing device 114 is disposed on a shoe of the user, but embodiments of the disclosure are not limited thereto. The second microcontroller unit 114a is used to control the second posture detection device 114b, the second communication device 114c, and the ranging device 114d. The second posture detection device 114b is used to detect a foot posture of the user, thereby obtaining a set of foot posture data. The ranging device 114d is used to measure a distance between the sensing position and an ambient object, thereby obtaining a set of distance measurement data. The second communication device 114c is used to transmit the set of foot posture data and the set of distance measurement data to the data server 130.

Figure 2:
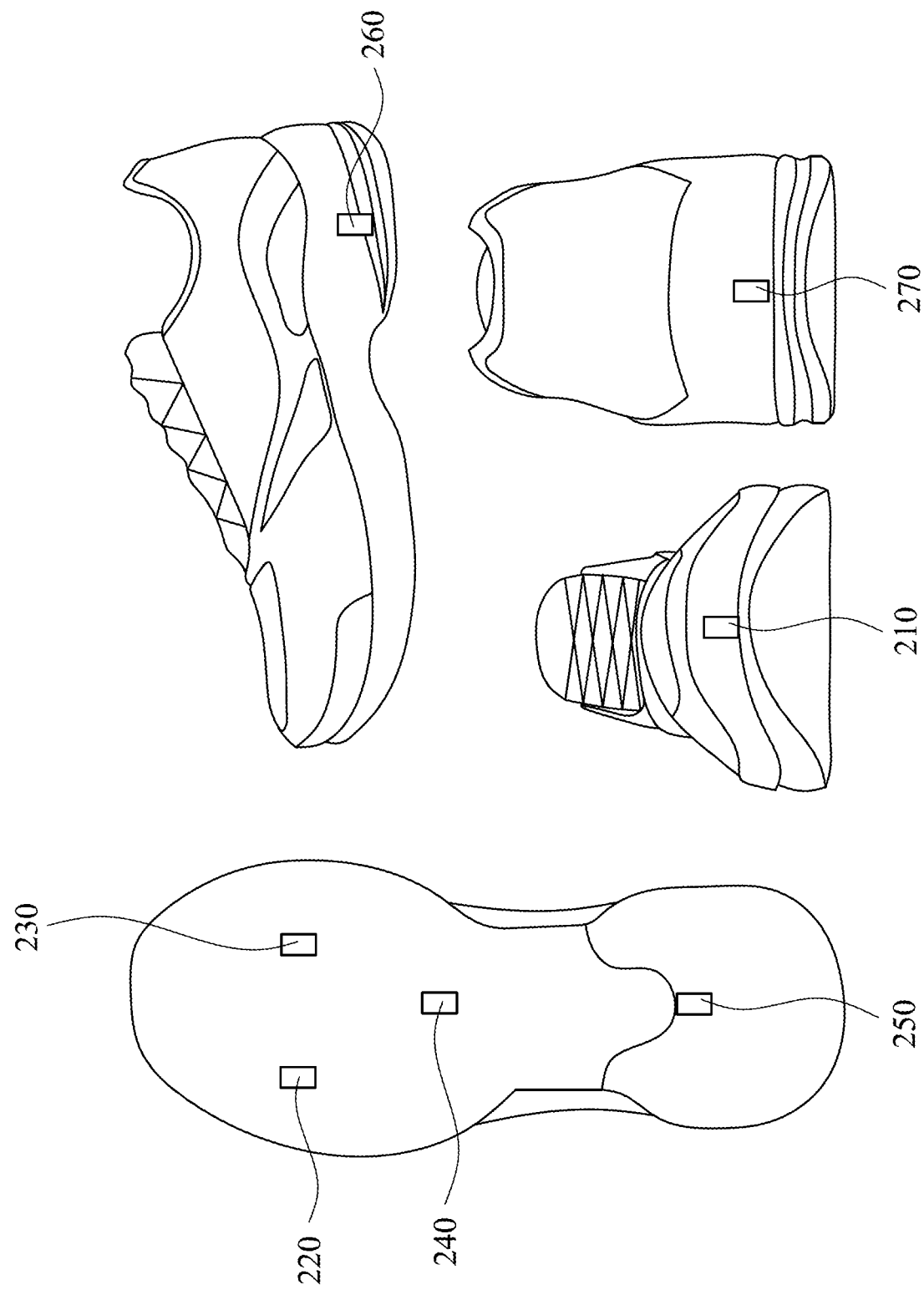
FIG. 2 is a schematic diagram showing locations of second sensing devices according to some embodiments of the disclosure.

Referring to FIG. 2, FIG. 2 is a schematic diagram showing locations of the second sensing devices 114 according to some embodiments of the disclosure. In the embodiments, there are seven second sensing devices 114 disposed on the shoe of the user, which are correspondingly disposed at a toe position 210 of the shoe, a left front sole position 220 of the shoe, a right front sole 230 of the shoe, a middle sole position 240 of the shoe, a rear sole position 250 of the shoe, an outsole position 260 of the shoe, and a heel position 270 of the shoe, in which the middle sole position 240 is located among the rear sole position 250, the left front sole position 220 and the right front sole position 230, and corresponds to an arch position of the user's foot. However, in other embodiments of the disclosure, fewer or more second sensing devices 114 may be disposed on the shoe. For example, in an embodiment of the disclosure, four second sensing devices 114 are disposed on the shoe of the user, which are disposed on the toe position 210, the middle sole position 240, the rear sole position 250 and the heel position 270.

The second sensing devices 114 of the embodiments can sense the postures at the respective positions of the shoe and the distances between the respective positions of the shoe and corresponding ambient objects. For example, the second sensing device 114 disposed at the toe position 210 can sense the distance between the toe position 210 and its front object and the posture of the user's foot at the toe position 210, thereby obtaining and sending a set of distance measurement data and a set of body part posture data corresponding to the toe position 210 to the data server 130.

For example, the second sensing device 114 disposed at the left front sole position 220 can sense the distance between the left front sole position 220 and its underneath object and the posture of the user's foot at the left front sole position 220, thereby obtaining and sending a set of distance measurement data and a set of body part posture data corresponding to the left front sole position 220 to the data server 130.

For example, the second sensing device 114 disposed at the right front sole position 230 can sense the distance between the right front sole position 230 and its underneath object and the posture of the user's foot at the right front sole position 230, thereby obtaining and sending a set of distance measurement data and a set of body part posture data corresponding to the right front sole position 230 to the data server 130.

For example, the second sensing device 114 disposed at the middle sole position 240 can sense the distance between the middle sole position 240 and its underneath object and the posture of the user's foot at the middle sole position 240, thereby obtaining and sending a set of distance measurement data and a set of body part posture data corresponding to the middle sole position 240 to the data server 130.

For example, the second sensing device 114 disposed at the rear sole position 250 can sense the distance between the rear sole position 250 and its underneath object and the posture of the user's foot at the rear sole position 250, thereby obtaining and sending a set of distance measurement data and a set of body part posture data corresponding to the rear sole position 250 to the data server 130.

For example, the second sensing device 114 disposed at the outsole position 260 can sense the distance between the outsole position 260 and its side object and the posture of the user's foot at the outsole position 260, thereby obtaining and sending a set of distance measurement data and a set of body part posture data corresponding to the outsole position 260 to the data server 130.

For example, the second sensing device 114 disposed at the heel position 270 can sense the distance between the heel position 270 and its rear object and the posture of the user's foot at the heel position 270, thereby obtaining and sending a set of distance measurement data and a set of body part posture data corresponding to the heel position 270 to the data server 130.

In the embodiments, the second posture detection device 114b may include an accelerator, a gyroscope, a magnetometer and/or a barometer for detecting postures of the user's body parts. The ranging device 114d may be a tof-based (Time of Flight) laser range sensor or an ultrasonic range sensor for measuring a distance between the second sensing device 114 and its ambient object. The second communication device 114c may send the set of posture data of the user's body part and the set of distance measurement data of a respective position of the shoe to the data server 130 by using a WiFi technique or an ultra-wideband (UWB) technique. However, embodiments of the disclosure are not limited thereto.

Figure 3:
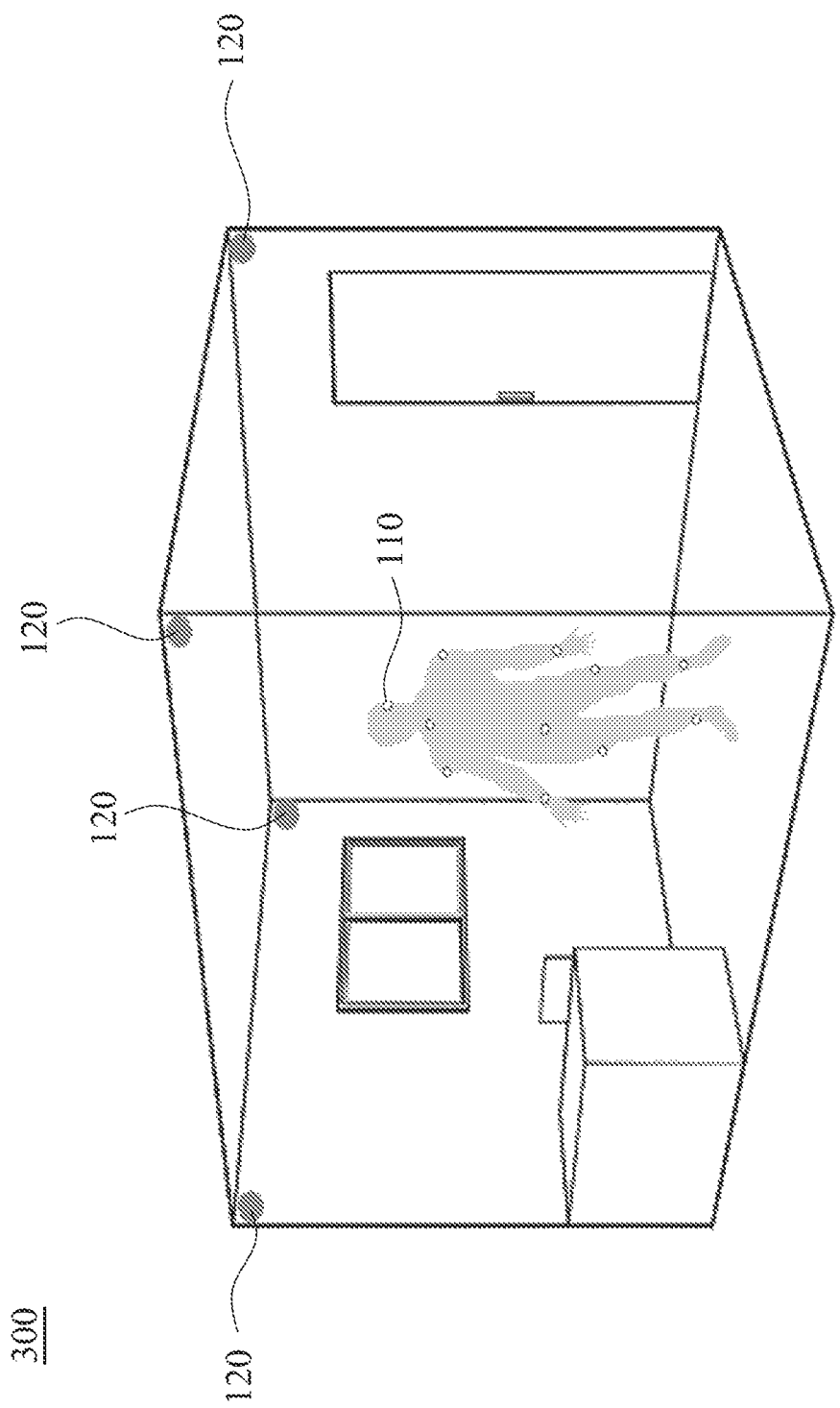
FIG. 3 is a schematic diagram showing locations of positioning devices according to some embodiments of the disclosure.

Referring to FIG. 1A and FIG. 3, FIG. 3 is a schematic diagram showing locations of the positioning devices 120 according to some embodiments of the disclosure. The positioning devices 120 are disposed in an activity space 300 of the user to detect a 3D position of each sensing device 110, thereby obtaining a set of body part position data corresponding to each sensing device 110. In the embodiments, each sensing device 110 uses a UWB positioning technique, and thus also includes an UWB positioning device (not shown), and may obtain its position via the positioning devices 120 in the activity space 300. In some embodiments of the disclosure, the positioning devices 120 use a WiFi technique, such that the sensing devices 110 can obtain their positions via the positioning devices 120 in the activity space 300 without needing additional positioning devices.

After the sensing devices 110 obtain corresponding sets of body part position data, the sets of body part position data are transmitted to the data sever 130 via the first communication devices 112c/the second communication devices 114c.

Referring back to FIG. 1A, the data server 130 is used to receive the sets of body part posture data, the sets of body part position data and/or the sets of distance measurement data for determining if the user falls down. For example, the data server 130 may provide three user statuses including a fall-down status, an about-to-fall (fall-like) status and a normal status. The data server 130 also uses the sets of body part posture data, the sets of body part position data and/or the sets of distance measurement data to determine the status of the user. Hereinafter, several embodiments are provided to explain how to determine the status of the user by using the data server 130.

In a first embodiment of the disclosure, the data server 130 computes skeleton information of the user according to the set of body part position and the set of body part posture data corresponding to each sensing device 110. Specifically, the data server 130 obtains the 3D positions of the corresponding body parts (such as the parts of head, hands, feet, trunk) of the user based on the body part position data of the sensing devices 110, and then the 3D positions of the corresponding body parts are used together with the body part posture data (such as rotational angles/acceleration speeds of the parts of head, hands, feet, trunk) to obtain the skeleton information including the 3D positions and postures of the corresponding body parts of the user. Thereafter, the data server 130 computes body posture information of the user according to the skeleton information. The body posture information is common body postures including but not limited to a leaning forward posture, a leaning backward posture, a standing posture and a sitting posture. When the user wears more wearable devices, the data server 130 may compute the body posture information of the user more accurately.

Then, the data server 130 performs a fall detection operation to determine if the user falls down based on the body posture information. For example, the data server 130 may determine if the acceleration speeds corresponding to the user's head and trunk are greater than a first predetermined acceleration threshold. When the acceleration speeds corresponding to the user's head and trunk are greater than the first predetermined acceleration threshold and the body posture information of the user indicates that the user is at a leaning status (such as the leaning forward or backward status), it is determined that the use is situated at the fall-down status. Further, When the acceleration speeds corresponding to the user's head and trunk are greater than the first predetermined acceleration threshold and the body posture information of the user indicates that the user is at a lie-down status, it is determined that the use is situated at the fall-down status.

For example, the data server 130 may determine if the acceleration speeds corresponding to the user's head and trunk are smaller than a first predetermined acceleration threshold and greater than a second predetermined acceleration threshold. When the acceleration speeds corresponding to the user's head and trunk are smaller than the first predetermined acceleration threshold and greater than the second predetermined acceleration threshold, and the body posture information of the user indicates that the user is at a leaning status, it is determined that the use is situated at the about-to-fall (fall-like) status.

For example, the data server 130 may determine if the acceleration speeds corresponding to the user's head and trunk are smaller than the second predetermined acceleration threshold. When the acceleration speeds corresponding to the user's head and trunk are smaller than the second predetermined acceleration threshold, and the body posture information of the user indicates that the user is not at a leaning status, it is determined that the use is situated at the normal status.

When determining that the user is situated at the fall-down status, the data server 130 issues a fall detection signal to the display device 140, and the display device 140 issues a warning message based on the fall detection signal. In the embodiments, the display device 140 may be an electronic device such as a smart watch, a smart glass, a notebook computer, a tablet computer or a personal digital assistant (PDA), and the fall detection signal may be used to notify a default contact person that the user has fallen down and needs help. Besides, when determining that the user is situated at the about-to-fall (fall-like) status, the data server 130 issues a fall detection signal to the display device 140, and the display device 140 issues a warning message based on the fall detection signal. In the embodiments, the display device 140 may be smart glasses of the user, which can notify the user that he or she has a risk of falling. Meanwhile, the data server 130 may record the data for doctor's analysis.

In a second embodiment of the disclosure, the data server 130 uses the sets of distance measurement data corresponding to the sensing devices 110 (the second sensing devices 114) to determine if the user falls down. For example, the distance measurement data returned by the second sensing devices 140 may have different waveforms corresponding to different user statuses, and accordingly, the data server 130 may determine if the user falls down. Referring to FIG. 2 and FIG. 4A to FIG. 4C, FIG. 4A to FIG. 4C are waveform diagrams of distance measurement data returned by the second sensing devices 114 when the user is at a status of normal walking, a status of stepping up stairs, and a status of stepping down stairs respectively, in which curve Tof1 shows the set of distance measurement data returned by the second sensing device 114 disposed at the toe position 210; curve Tof2 shows the set of distance measurement data returned by the second sensing device 114 disposed at the left front sole position 220; curve Tof4 shows the set of distance measurement data returned by the second sensing device 114 disposed at the middle sole position 240; curve Tof5 shows the set of distance measurement data returned by the second sensing device 114 disposed at the rear sole position 250; curve Tof6 shows the set of distance measurement data returned by the second sensing device 114 disposed at the outsole position 260; and curve Tof7 shows the set of distance measurement data returned by the second sensing device 114 disposed at the heel position 270.

Figure 4A:
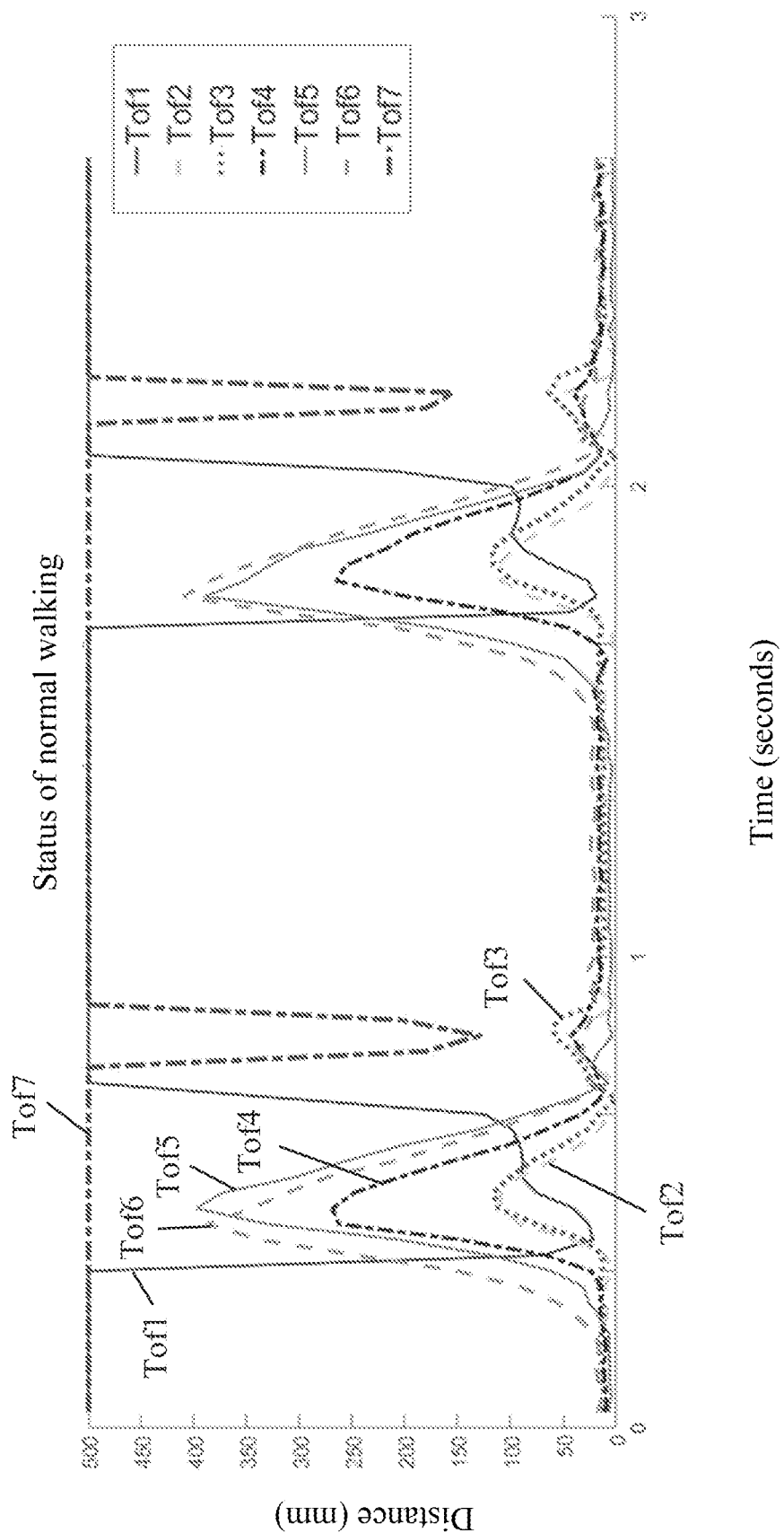
FIG. 4A to FIG. 4C are waveform diagrams of distance measurement data returned by the second sensing devices when a user is at a status of normal walking, a status of stepping up stairs, and a status of stepping down stairs respectively.
Figure 4B:
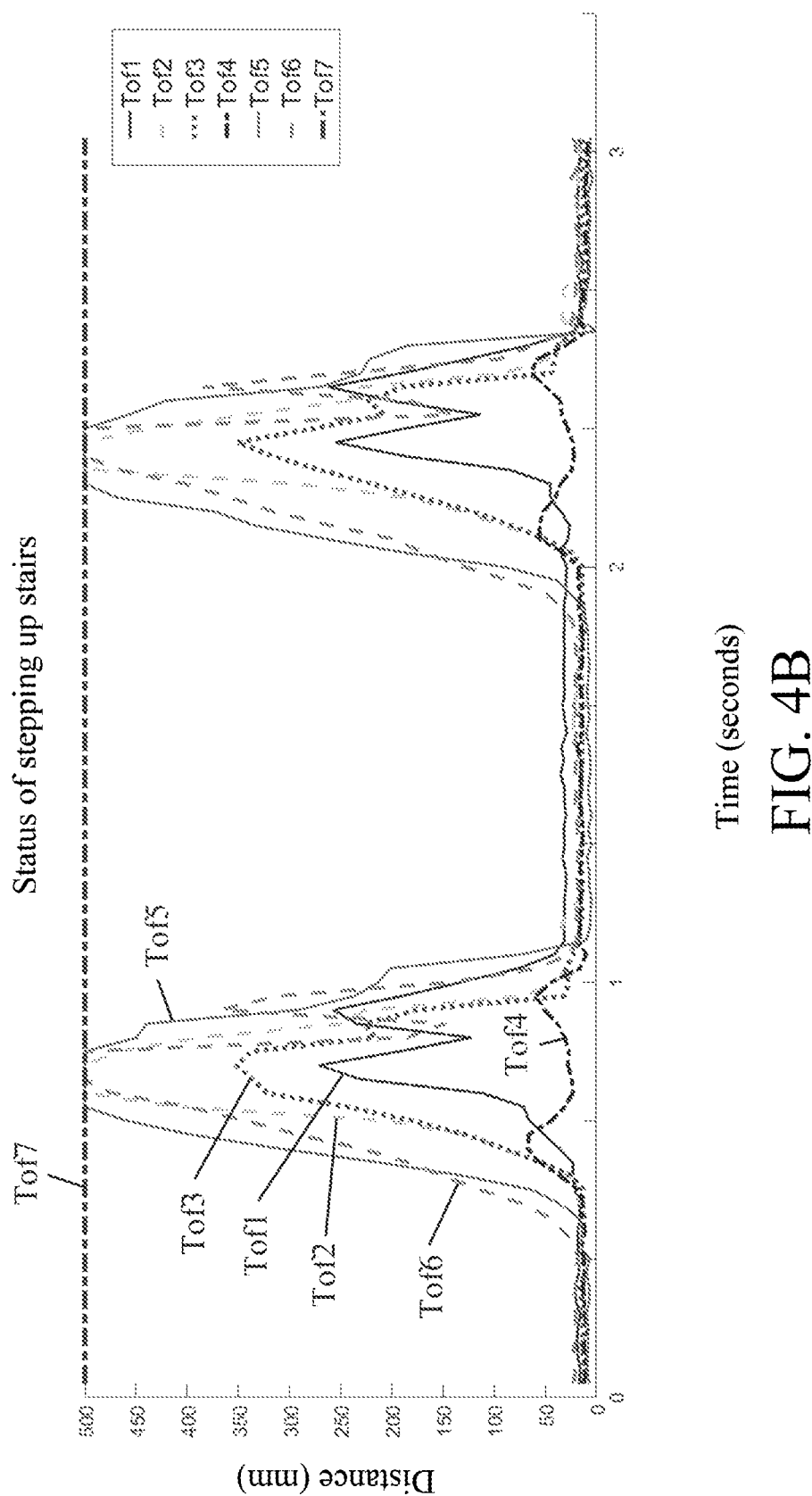
Figure 4C:
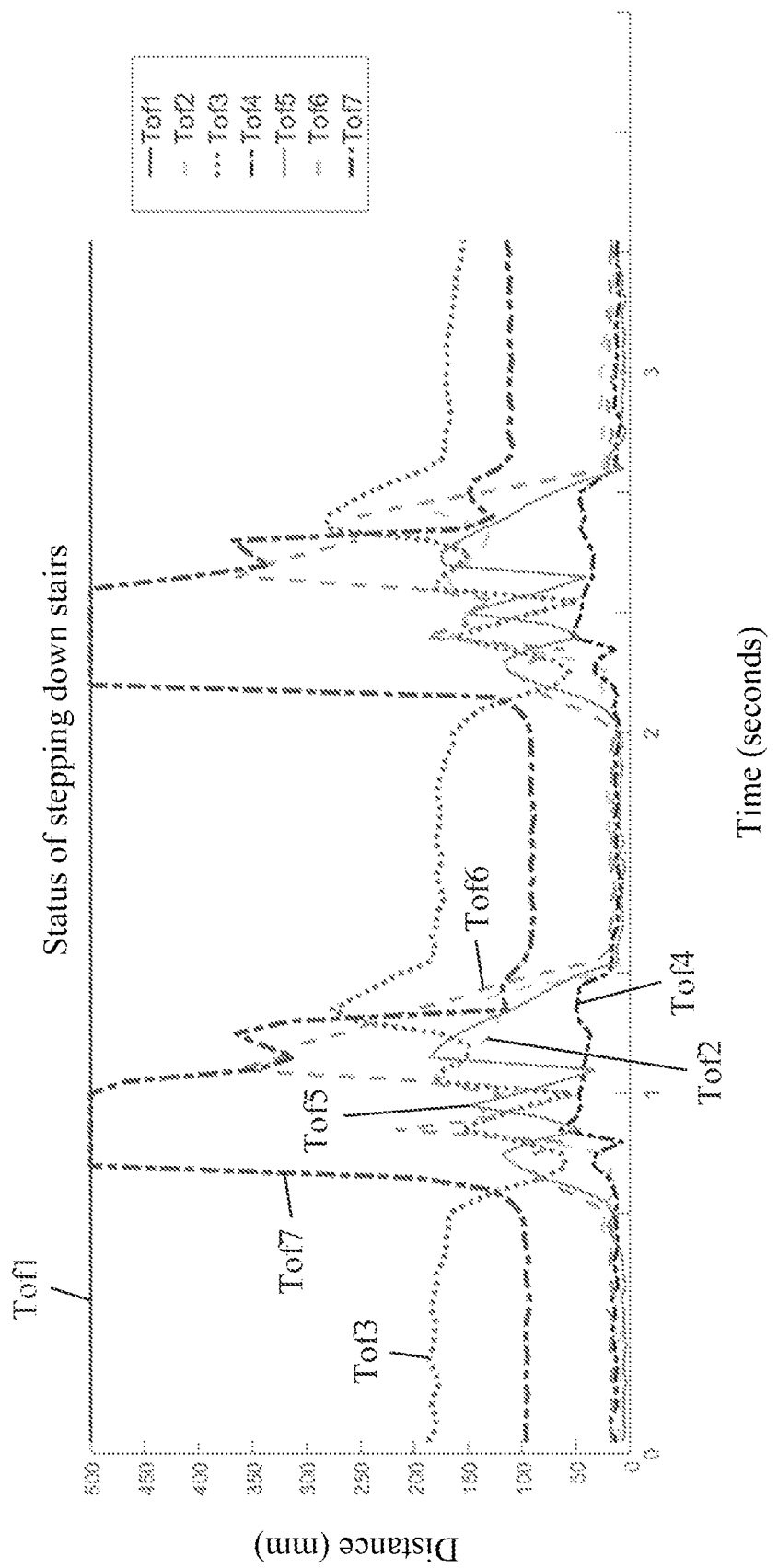

As shown in FIG. 4A to FIG. 4C, when the user is at a status of normal walking or stepping up or down stairs. Curves Tof1-Tof7 overall have stable periodic changes. As shown in FIG. 4A, curve Tof5 (the rear sole position) changes more dramatically than curve Tof4 (the arch position) and has obvious step transitions, and thus can be used as a waveform feature of normal walking. As shown in FIG. 4B, the distance measurement values (curves Tof1-Tof7) all change when the user raises his or her foot, and have significant differences from top to bottom, and thus can be used as a waveform feature of stepping up stairs. As shown in FIG. 4C, the distance measurement values of curve Tof2 (the left front sole position 220) and curve Tof3 (the right front sole position 220) are greater than those of curve Tof5 (the rear sole position) in the initial moving stage (for example about two seconds), and thus can be used as a waveform feature of stepping down stairs.

Figure 4D:
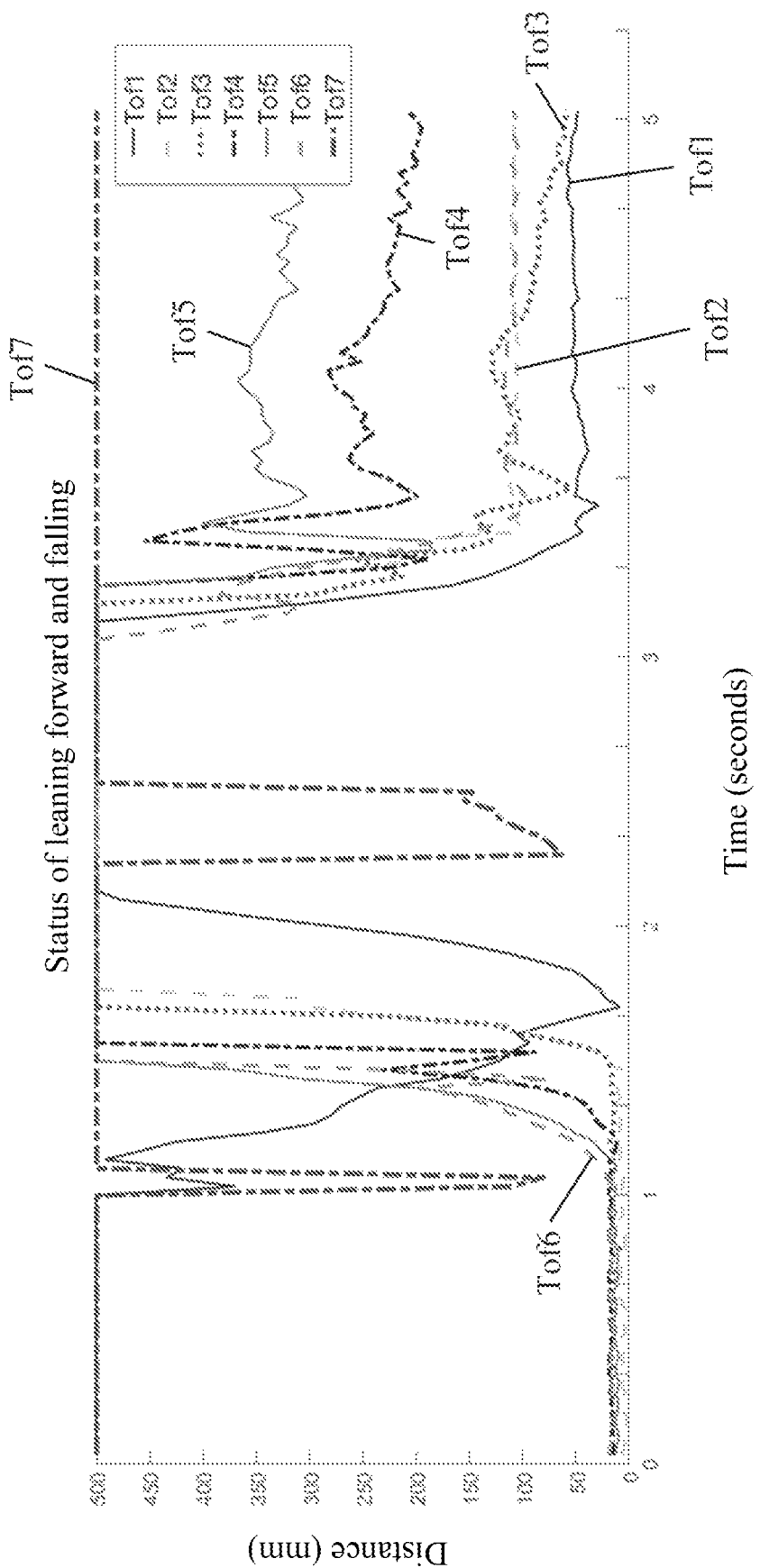
FIG. 4D to FIG. 4F are waveform diagrams of distance measurement data returned by the second sensing devices when a user is at a status of leaning forward and falling, a status of missing footing and falling, and a status of stumbling and falling respectively.
Figure 4E:
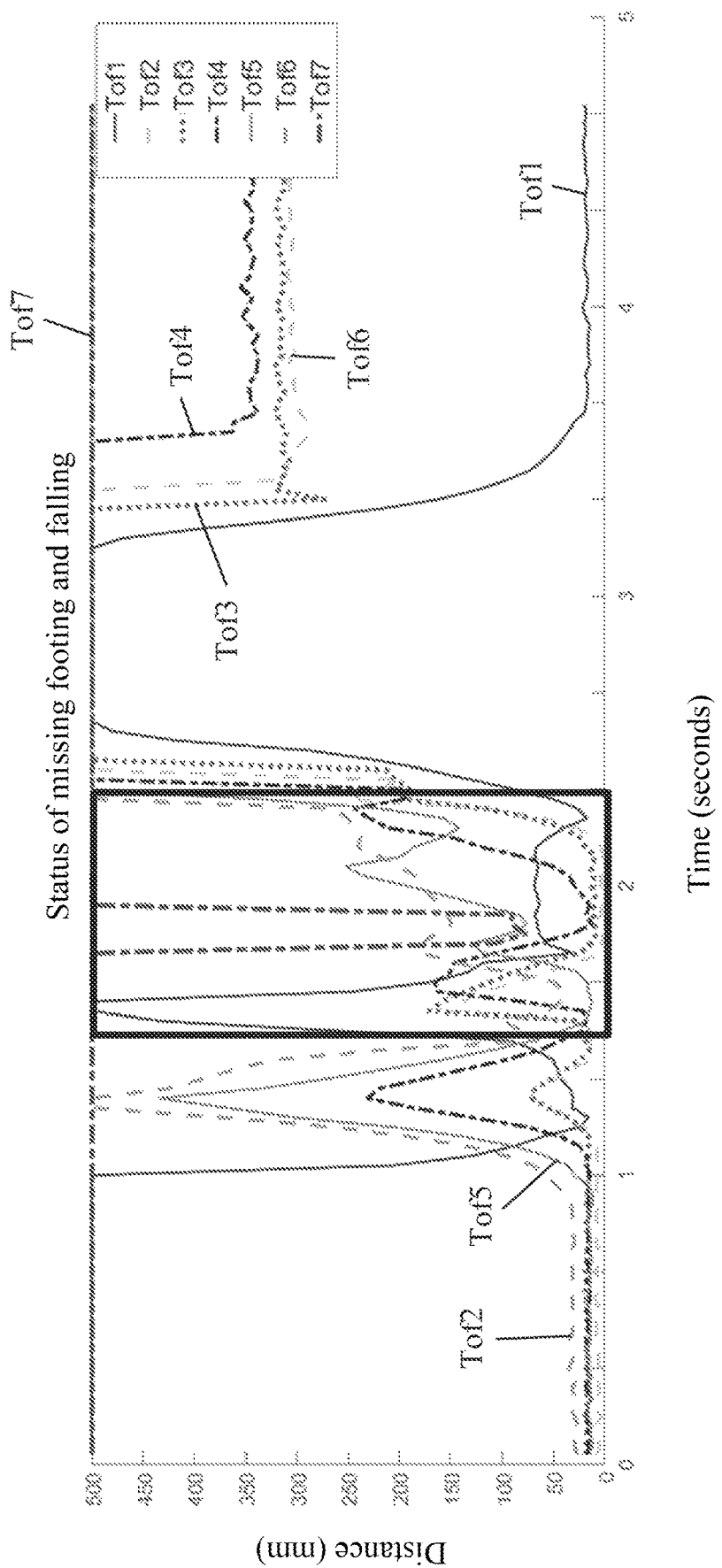
Figure 4F:
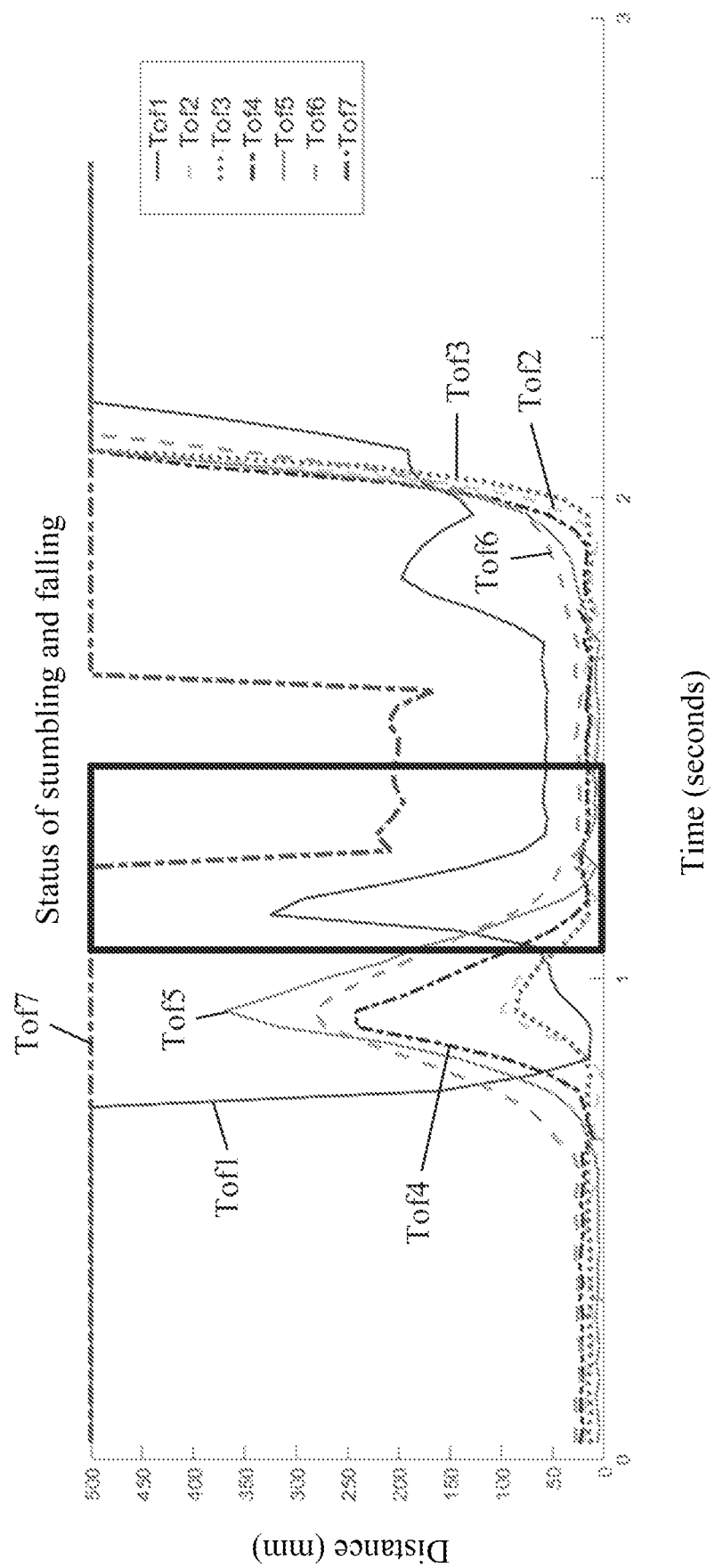

Referring to FIG. 4D to FIG. 4F, FIG. 4D to FIG. 4F are waveform diagrams of distance measurement data returned by the second sensing devices 114 when a user is at a status of leaning forward and falling, a status of missing footing and falling, and a status of stumbling and falling respectively. As shown in FIG. 4D, during the period long after the falling down of the user, the distance measurement values returned by the second sensing devices 114 all are at saturated states (i.e. maximum measurable values), and during the falling down of the user, curve Tof5 (the rear sole position) has the most significant changes within a short period of time and thus can be used as a waveform feature of the user at the state of leaning forward and falling. Moreover, the changes of the distance measurement values from top to bottom within a short period of time also can be used to determine the falling-down status in forward, backward, left and right directions. As shown FIG. 4E, normal walking is shown in the initial period of moving, but the distance measurement values all have dramatic changes (as shown in a rectangular frame of FIG. 4E) before the falling down of the user, which thus can be used as a waveform feature of the user at a status of missing footing and falling. As shown FIG. 4F, normal walking is shown in the initial period of moving (such as before 60 seconds), but curve Tof1 has small peak signals (as shown in a rectangular frame of FIG. 4F) before the falling down of the user, which thus can be used as a waveform feature of the user at a status of stumbling and falling.

The waveform feature can be shown by a mean value, a kurtosis value, a variance, a difference or sum between the values from two second sensing devices 114, and can be processed by various feature retrieving methods. For example, a time window is defined by a predetermined period of time (such as 1-3 seconds), and is used to retrieve features from the distance measurement data returned by the second sensing devices 114.

It can be known from the above that the data server 130 of the second embodiment retrieves a waveform feature from the distance measurement data returned by the second sensing devices 114, and determines if the user falls down according to the waveform feature retrieved. Specifically, if the waveform feature retrieved is similar to the waveform feature when the user is at a status of leaning and falling, missing foot and falling or stumbling and falling, it is determined that the user falls down. When determining that the user is situated at the fall-down status, the data server 130 issues a fall detection signal to the display device 140, and the display device 140 issues a warning message based on the fall detection signal.

Moreover, in the second embodiment, the data server 130 may also use the distance measurement data and the foot posture data returned by the second sensing devices 114 to determine if the user falls down. For example, the foot posture includes pitch and roll angle data of the user's foot, and the second embodiment may use the pitch and roll angle data to determine if the user falls down.

Considering the pitch angle, it is determined that the user falls down when the pitch angle increases to 90 degrees continuously or decreases to −90 degrees continuously and then is kept at 90 degrees or −90 degrees subsequently. Further, when the roll angle increases to 90 degrees continuously or decreases to −90 degrees continuously and then is kept at 90 degrees or −90 degrees subsequently, it is determined that the user falls down.

In a third embodiment of the disclosure, the data server 130 may include an artificial intelligence device, which can use the data from the sensing devices 110 to determine the user is at the fall-down status, the about-to-fall (fall-like) status or the normal status. The input data received by the artificial intelligence device includes reading values of an accelerator, a gyroscope, a magnetometer and/or a barometer of the sensing devices 110, and reading values of a range sensor of the sensing devices. By using the determining method of the first or second embodiment, the artificial intelligence device of the data server 130 can determine if the use is situated at the fall-down status, about-to-fall (fall-like) status or the normal status.

In the embodiments, the artificial intelligence device may adopt a support vector machine (SVM) algorithm, a convolutional Neural Network (CNN) algorithm, a k-nearest (k-NN) neighbors algorithm or a recurrent neural network (RNN) algorithm. However, embodiments of the disclosure are not limited thereto.

Figure 5A:
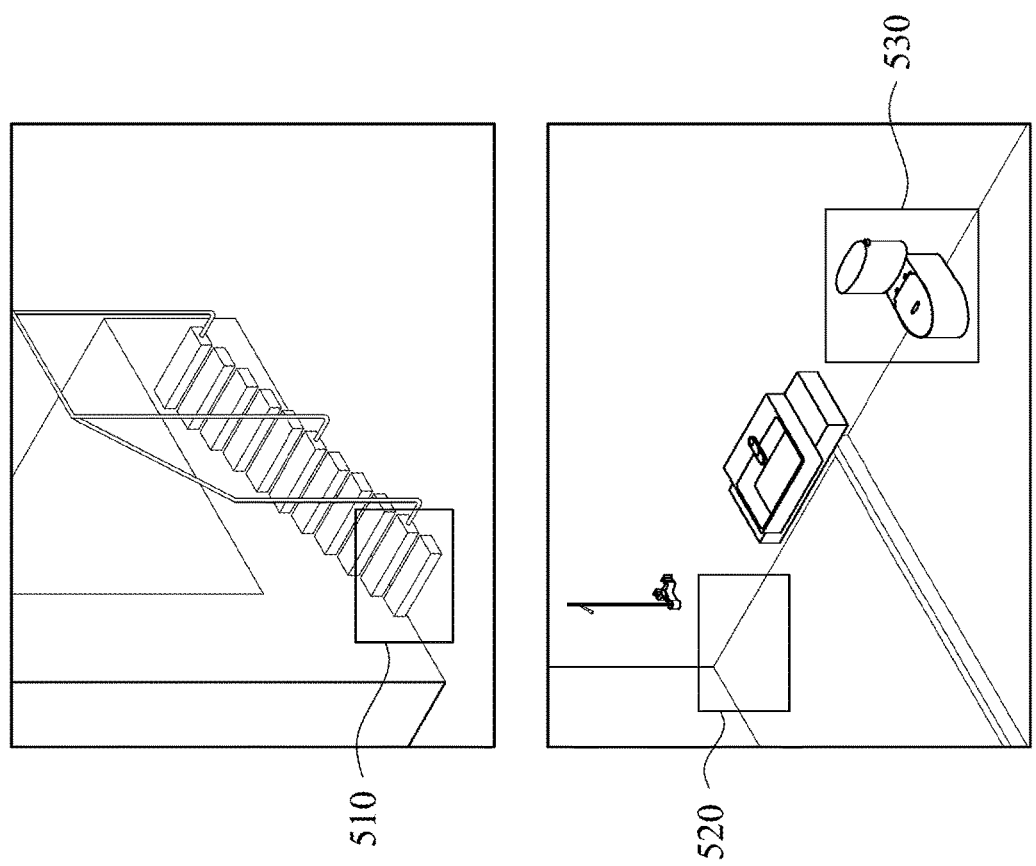
FIG. 5A and FIG. 5B are schematic diagrams showing sub-spaces of an activity space.
Figure 5B:
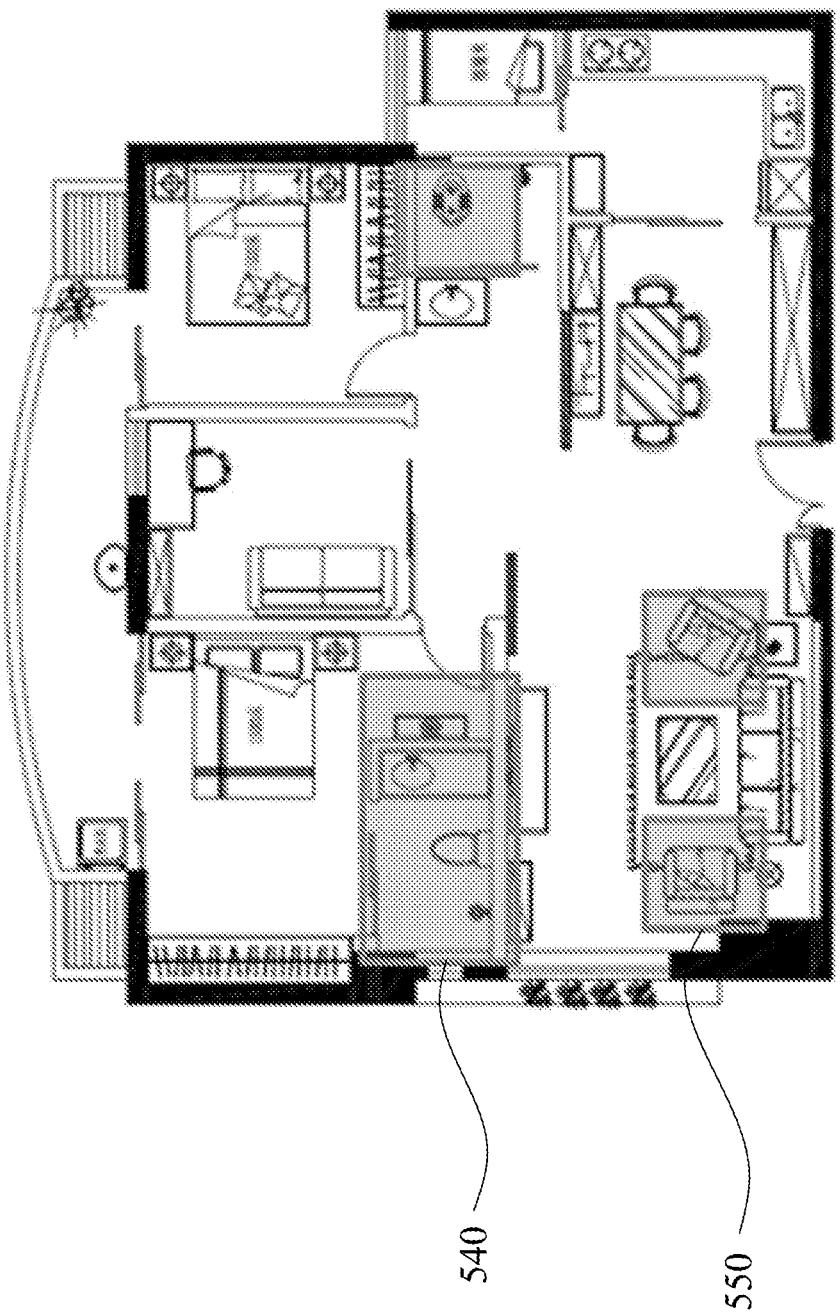

Moreover, the input data of the artificial intelligence device may further include a set of space risk level data pre-stored in the data server 130. The set of space risk level data includes plural risk levels in respective sub-spaces of the activity space of the user. As shown FIG. 5A, the sub-space risk levels may be evaluated with respect to physical spaces. For example, a sub-space 410 is directed to stairs, and thus is given with a higher risk level. A sub-space 420 is directed to a shower room, and thus is given with a higher risk level. A sub-space 430 is directed to a toilet, and thus is given with a higher risk level. As shown FIG. 5B, the sub-space risk levels may be evaluated with respect to a plane diagram of the activity space. For example, a sub-space 440 is directed to a bath room, and thus is given with a higher risk level. A sub-space 450 is directed to a sofa, and thus is given with a lower risk level.

As such, the data server 130 may determine if the user falls down with reference to the risk level corresponding to the user's location.

Further, the data server 130 also may give different weights on different input data according to the risk levels corresponding to the user's locations. For example, when the user is in a sub-space 410 (stairs), a greater weight would be given to the reading values of the ranger sensors. On the other hand, when the user enters a sub-space with a higher risk level, the sensing devices 110 would be controlled to raise their sampling rates.

It is worthy to be noted that the sensing device 110 of the disclosure includes a feedback device for providing a feedback from the user's sense. If the user fails to respond within a period of time (for example, deactivates the feedback device), it indicates that the user has an accident. The feedback device can be such as a motor vibration device or a speaker, which can provide a vibration feedback or a sound feedback to the user.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fall detection system for detecting a user's fall within an activity space, the fall detection system comprising:
   a plurality of sensing devices each of which is disposed on a sensing position of a shoe of the user, each of the sensing devices comprising:
      a ranging device configured to measure a distance between the sensing position and an ambient object, thereby obtaining a set of distance measurement data; and
      a communication device configured to transmit the set of distance measurement data;

a data server configured to receive the set of distance measurement data of each of the sensing devices and perform a fall detection operation to determine if the user falls down according to the set of distance measurement data, wherein the data server issues a fall detection signal when it is determined that the user falls down; and a display device configured to receive the fall detection signal and display a warning message in accordance with the fall detection signal.

2. The fall detection system of claim 1, wherein a first one of the sensing devices is disposed on a toe of the shoe of the user, a second one of the sensing devices is disposed on a heel of the shoe of the user, a third one of the sensing devices is disposed on a front sole of the shoe of the user, and a fourth one of the sensing devices is disposed on a rear sole of the shoe of the user.

3. The fall detection system of claim 1, wherein a first one of the sensing devices is disposed on a toe of the shoe of the user, a second one of the sensing devices is disposed on a left front sole of the shoe of the user, a third one of the sensing devices is disposed on a right front sole of the shoe of the user, a fourth one of the sensing devices is disposed adjacent to the second one and the third one of the sensing devices, a fifth one of the sensing devices is disposed on a rear sole of the shoe of the user, a sixth one of the sensing devices is disposed on a lateral side of the shoe of the user, a seventh one of the sensing devices is disposed on a heel of the shoe of the user, and the fourth one of the sensing devices is disposed among the fifth one, the second one and the third one of the sensing devices.

4. A fall detection system for detecting a user's fall within an activity space, the fall detection system comprising:

a plurality of sensing devices each of which is disposed on a sensing position of a shoe of the user, each of the sensing devices comprising:

a ranging device configured to measure a distance between the sensing position and an ambient object, thereby obtaining a set of distance measurement data; and a communication device configured to transmit the set of distance measurement data;

a data server configured to receive the set of distance measurement data of each of the sensing devices and perform a fall detection operation in accordance with a waveform feature of the set of distance measurement data of each of the sensing devices to determine if the user falls down according to the set of distance measurement data, wherein the data server issues a fall detection signal when it is determined that the user falls down; and a display device configured to receive the fall detection signal and display a warning message in accordance with the fall detection signal;

wherein a first one of the sensing devices is disposed on a toe of the shoe of the user, and a second one of the sensing devices is disposed on a heel of the shoe of the user.

5. The fall detection system of claim 4, wherein a third one of the sensing devices is disposed on a front sole of the shoe of the user, and a fourth one of the sensing devices is disposed on a rear sole of the shoe of the user.

6. The fall detection system of claim 4, wherein a third one of the sensing devices is disposed on a right front sole of the shoe of the user, a fourth one of the sensing devices is disposed adjacent to the second one and the third one of the sensing devices, a fifth one of the sensing devices is disposed on a rear sole of the shoe of the user, a sixth one of the sensing devices is disposed on a lateral side of the shoe of the user, a seventh one of the sensing devices is disposed on a left front sole of the shoe of the user, and the fourth one of the sensing devices is disposed among the fifth one, the second one and the third one of the sensing devices.

7. The fall detection system of claim 4, wherein the waveform feature is shown by a mean value, a kurtosis value, a variance, a difference or sum between the values from two of the sensing devices.

8. The fall detection system of claim 7, wherein the waveform feature is retrieved by using a time window defined by a predetermined period of time.

* * * * *